(12) United States Patent
Johansson et al.

(10) Patent No.: US 11,129,530 B2
(45) Date of Patent: Sep. 28, 2021

(54) EYE TRACKING USING EYEBALL CENTER POSITION

(71) Applicant: Tobii AB, Danderyd (SE)

(72) Inventors: Simon Johansson, Danderyd (SE); Mark Ryan, Danderyd (SE)

(73) Assignee: Tobii AB, Danderyd (SE)

( * ) Notice: Subject to any disclaimer, the term of this patent is extended or adjusted under 35 U.S.C. 154(b) by 467 days.

(21) Appl. No.: 16/124,918

(22) Filed: Sep. 7, 2018

(65) Prior Publication Data

US 2019/0076015 A1 Mar. 14, 2019

Related U.S. Application Data

(60) Provisional application No. 62/556,086, filed on Sep. 8, 2017.

(51) Int. Cl.
| | | |
|---|---|---|
| *A61B 3/113* | (2006.01) | |
| *A61B 3/11* | (2006.01) | |
| *G06K 9/00* | (2006.01) | |
| *G02B 27/00* | (2006.01) | |
| *G02B 27/01* | (2006.01) | |
| *A61B 3/00* | (2006.01) | |
| *A61B 3/14* | (2006.01) | |
| *A61B 5/00* | (2006.01) | |

(52) U.S. Cl.
CPC ............ *A61B 3/113* (2013.01); *A61B 3/0008* (2013.01); *A61B 3/11* (2013.01); *A61B 3/14* (2013.01); *G02B 27/0093* (2013.01); *G02B 27/017* (2013.01); *G06K 9/0061* (2013.01); *G06K 9/00604* (2013.01); *A61B 3/0025* (2013.01); *A61B 5/6803* (2013.01); *G02B 2027/014* (2013.01); *G02B 2027/0118* (2013.01); *G02B 2027/0187* (2013.01); *G06T 2207/30201* (2013.01)

(58) Field of Classification Search
CPC ... A61B 3/113; G06K 9/0061; G06K 9/00604
USPC .................................................. 351/209–211
See application file for complete search history.

(56) References Cited

U.S. PATENT DOCUMENTS

| | | | |
|---|---|---|---|
| 7,572,008 | B2 | 8/2009 | Elvesjo et al. |
| 9,041,787 | B2 | 5/2015 | Andersson et al. |
| 2010/0013949 | A1 | 1/2010 | Miyamoto |
| 2018/0267323 | A1* | 9/2018 | Tsurumi ............. G02B 27/0179 |

FOREIGN PATENT DOCUMENTS

| | | |
|---|---|---|
| EP | 2467053 A1 | 6/2012 |
| EP | 3228238 A1 | 10/2017 |
| WO | 2016/088418 A1 | 6/2016 |

\* cited by examiner

*Primary Examiner* — James C. Jones
(74) *Attorney, Agent, or Firm* — Samuel Yamron (57) ABSTRACT

An eye tracking system having circuitry configured to perform a method is disclosed. An estimated radius (r) from an eyeball center to a pupil center in an eye is obtained, and an estimated eyeball center position (e) in the eye in relation to an image sensor for capturing images of the eye is determined, and an image of the eye captured by means of the image sensor, and a position of a representation of the pupil center in the eye in the obtained image is identified. An estimated pupil center position (p') is then determined based on the estimated eyeball center position (e), the estimated radius (r), and the identified position of the representation of the pupil center in the obtained image.

16 Claims, 7 Drawing Sheets

EYE TRACKING USING EYEBALL CENTER POSITION

CROSS-REFERENCE TO RELATED APPLICATIONS

This application claims priority to and the benefit of U.S. Provisional Patent Application No. 62/556,086, filed Sep. 8, 2017, the entire disclosure of which is incorporated by reference herein for all purposes.

BRIEF SUMMARY OF THE INVENTION

In one embodiment, a method is disclosed. The method may include obtaining an estimated radius (r) from an eyeball center to a pupil center in an eye. The method may also include determining an estimated eyeball center position (e) in the eye in relation to an image sensor for capturing images of the eye. The method may additionally include obtaining an image of the eye captured by means of the image sensor. The method may further include identifying a position of a representation of the pupil center in the eye in the obtained image. The method may moreover include determining an estimated pupil center position (p') based on the estimated eyeball center position (e), the estimated radius (r), and the identified position of the representation of the pupil center in the obtained image.

In another embodiment, a computer-readable storage media is disclosed. When executed by a computing system that implements eye/gaze data processing, executable instructions in the storage media may perform a method. The method may include obtaining an estimated radius (r) from an eyeball center to a pupil center in an eye. The method may also include determining an estimated eyeball center position (e) in the eye in relation to an image sensor for capturing images of the eye. The method may further include obtaining an image of the eye captured by means of the image sensor. The method may additionally include identifying a position of a representation of the pupil center in the eye in the obtained image. The method may moreover include determining an estimated pupil center position (p') based on the estimated eyeball center position (e), the estimated radius (r), and the identified position of the representation of the pupil center in the obtained image.

BRIEF DESCRIPTION OF THE DRAWINGS

All the figures are schematic and generally only show parts which are necessary in order to elucidate the respective embodiments, whereas other parts may be omitted or merely suggested.

DETAILED DESCRIPTION OF THE INVENTION

The ensuing description provides exemplary embodiments only, and is not intended to limit the scope, applicability, or configuration of the disclosure. Rather, the ensuing description of the exemplary embodiments will provide those skilled in the art with an enabling description for implementing one or more exemplary embodiments. It being understood that various changes may be made in the function and arrangement of elements without departing from the spirit and scope of the invention as set forth herein.

For example, any detail discussed with regard to one embodiment may or may not be present in all contemplated versions of that embodiment. Likewise, any detail discussed with regard to one embodiment may or may not be present in all contemplated versions of other embodiments discussed herein. Finally, the absence of discussion of any detail with regard to embodiment herein shall be an implicit recognition that such detail may or may not be present in any version of any embodiment discussed herein.

Specific details are given in the following description to provide a thorough understanding of the embodiments. However, it will be understood by one of ordinary skill in the art that the embodiments may be practiced without these specific details. For example, circuits, systems, networks, processes, and other elements in the invention may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process may be terminated when its operations are completed, but could have additional steps not discussed or included in a figure. Furthermore, not all operations in any particularly described process may occur in all embodiments. A process may correspond to a method, a function, a procedure, a subroutine, a subprogram, etc. When a process corresponds to a function, its termination corresponds to a return of the function to the calling function or the main function.

The term "machine-readable medium" or the like includes, but is not limited to transitory and non-transitory, portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments of the invention may be implemented, at least in part, either manually or automatically. Manual or automatic implementations may be executed, or at least assisted, through the use of machines, hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

The present disclosure generally relates to the field of eye tracking. In particular, the present disclosure relates to systems and methods for use in generating gaze tracking data indicating an eye direction and/or gaze direction of an eye.

Several different eye tracking systems are known in the art. Such systems may for example be employed to identify a location at a display at which a user is looking and/or the gaze direction of the user. Some eye tracking systems capture images of at least one of a user's eyes, and then employ image processing to extract key features from the eye, such as a pupil center together with glints (corneal reflections) from illuminators illuminating the eye. The extracted features may then be employed to determine where at a display the user is looking, the eye direction of the user and/or the gaze direction of the user.

One known method of eye tracking includes the use of infrared light and an image sensor. The infrared light is directed towards the pupil of a user and the reflection of the light is captured by an image sensor. Through analysis of the reflection point, the direction of the user's gaze may be calculated. One such system is described in U.S. Pat. No. 7,572,008 (which is hereby incorporated by reference in its entirety).

Portable or wearable eye tracking devices have also been previously described. One such eye tracking system is described in U.S. Pat. No. 9,041,787 (which is hereby incorporated by reference in its entirety). A wearable eye tracking device is described using illuminators and image sensors for determining gaze direction.

In applications of eye tracking for in portable or wearable eye tracking devices, such as in virtual reality (VR) devices and augmented reality (AR) devices, where head mounted devices are used which include an eye tracking system determining an eye direction and/or gaze direction based on a pupil center and glints from illuminators illuminating a user's eyes, situations can arise where a user's eyes are directed in relation to illuminators such that no or too few glints can be identified for eye tracking, or the glint or glints identified are difficult to pair with the respective illuminator causing the glint. In such situations it will be difficult or impossible to determine eye direction and/or gaze direction and or eye direction or at least not with desirable reliability.

It would be desirable to provide an eye tracking technology to account for such situations where with no or too few glints identified for eye tracking, or that the glint or glints identified are difficult to correlate to the illumination rays.

An object of the present disclosure is to address at least one of the issues described above.

According to a first aspect, there is provided a method comprising obtaining an estimated radius from an eyeball center to a pupil center in an eye, and determining an estimated eyeball center position in the eye in relation to an image sensor for capturing images of the eye. Furthermore, an image of the eye captured by means of the image sensor is obtained and a position of a representation of the pupil center in the eye in the obtained image is determined. Finally, an estimated pupil center position is determined based on the estimated eyeball center position, the estimated radius, and the identified position of the representation of the pupil center in the obtained image.

In some situations, a primary method for determining eye direction and/or gaze direction of an eye fails to provide reliable results. This may be caused by a current eye direction or other temporary factors affecting the possibility for the method to provide reliable results of eye direction and/or gaze direction. For some applications of eye tracking, another method based on an estimated eyeball center position can then be used instead of the primary method for determining an eye direction in such situations. More specifically, such methods using an estimated eyeball center position can be used in applications of eye tracking where the eyeball center position can be approximated to be constant in relation to an image sensor capturing images of the eye regardless of eye direction. The approximation will be valid at least for some period of time.

The estimated eyeball center position may be determined in a situation where it is possible for it to be determined with required reliability. The estimated eyeball center position may for example be determined based on the primary method for determining eye tracking and/or gaze tracking. However, it will be appreciated that any other method can be used as long as estimated eyeball center position may be determined with required reliability.

When the estimated eyeball center position has been determined, this estimation can then be used for situations when it is not possible to determine the eye direction and/or gaze direction with required reliability based on the primary method. An image of the eye captured by means of the image sensor is obtained and a position of a representation of the pupil center in the eye in the obtained image is determined. An estimated radius from an eyeball center to a pupil center of an eye is obtained. The estimated radius is an approximation of the distance from the eyeball center to the pupil center of a human eye. As the estimated eyeball center position in relation to the image sensor is known, and the estimated radius from the eyeball center to the pupil center is known, these can be combined with the identified representation of the pupil center in the image captured by the image sensor to determine an estimated pupil center position.

The determined pupil center position is the actual position of the pupil center in relation to the image sensor.

The image sensor can be any type of imaging sensor consisting of an integrated circuit containing an array of pixel sensors, each pixel containing a photodetector and an active amplifier. The image sensor is capable of converting light into digital signals. In reality, as an example, it could be:

Infrared image sensor or IR image sensor
RGB sensor
RGBW sensor
RGB or RGBW sensor with IR filter The shutter mechanisms of the image sensors can be either rolling shutter or global shutter.

In embodiments, the estimated radius is first selected as the approximation of the distance from the eyeball center to the pupil center of a human eye. When further data regarding the eyes of a current user are retrieved the estimated radius can be updated.

In embodiments implemented in a system where a primary method for determining eye direction and/or gaze direction of an eye is based on determining a pupil center in the eye and glints (corneal reflections) on the eye from one or more illuminators illuminating the eye, an example of a situation where a primary method does not provide reliable results, is when an angle between a direction of the eye in relation to one or more illumination rays from the one or more illuminators becomes large, e.g. when the eye is directed to points at the edge of a display of the system. In such a situation difficulties may arise in identifying any glints or at least a sufficient number of glints on the eye, and in particular on a cornea of the eye, or that an identified glint or identified glints cannot be associated to a corresponding illuminator of the one or more illuminators. In such a situation it may not be possible to determine with required reliability an eye direction and/or gaze direction of the eye based on the identified glint or glints using the primary method.

One example of an application of eye tracking where another method based on an estimated eyeball center position can be used instead of the primary method for determining an eye direction in situations where the primary method fails is wearable devices, such as devices for VR and AR, where one or more image sensors are positioned on or in the wearable device, and hence, will not move in relation to the eyes when the user moves as long as the user is wearing the device. In such an application, an eyeball center position can be approximated to be constant in relation to an image sensor capturing images of the eye regardless of the eye direction and head position.

For wearable devices, such as devices for VR and AR, with a primary method for determining eye direction and/or gaze direction of an eye is based on determining a pupil center of and glints on the eye from one or more illuminators illuminating the eye, an estimated eyeball center position in the eye in relation to an image sensor for capturing images of the eye can for example be determined for a situation where sufficient number of glints are identified on the eye, and the glint or glints identified can be associated to the corresponding illuminator or illuminators, such that it is possible to determine the estimated eyeball center position with required reliability. For a situation where the primary method cannot identify any glints or at least not a sufficient number of glints on the eye, or where an identified glint or identified glints cannot be associated to a corresponding illuminator of the one or more illuminators, a method based on the estimated eyeball center position can be used to determine an eye direction and/or gaze direction.

Once the estimated pupil center position has been determined, according to some embodiments, an estimated eye direction is determined based on a vector from the estimated eyeball center position to the estimated pupil center position.

Furthermore, according to some embodiments, an estimated gaze direction is determined based on the estimated eye direction.

According to some embodiments, an estimated distance from a cornea sphere center in the eye to the pupil center and an estimated distance from the eyeball center to the cornea sphere center are obtained. The estimated radius from the eyeball center to the pupil center is then equal to the sum of the estimated distance from the cornea sphere center to the pupil center and the estimated distance from the eyeball center to the cornea sphere center.

The cornea of the eye is typically approximately spherical in a central region of the cornea located around the pupil, but deviates more from the spherical shape further away from the center of the cornea. The central region of the cornea may therefore be referred to as a spherical region, while the region of the cornea outside the spherical region may be referred to as a non-spherical region. The cornea sphere center is defined as a position at the center of an imaginary sphere of which the spherical region of the cornea forms part.

The estimated distance from the cornea sphere center to the pupil center, also known as pupil depth, can be a constant approximation or may be dynamically updated.

For example, in embodiments implemented in a system using a primary method for determining eye direction and/or gaze direction of an eye based on determining a pupil center in the eye and glints on the eye from one or more illuminators illuminating the eye, a position of the cornea sphere center is determined for a situation where there are sufficient number of glints on the eye, and the glint or glints identified can be associated to the corresponding illuminator of the one or more illuminators, such that it is possible to determine with required reliability the position of the cornea sphere center. From this the distance from the cornea center to the pupil center can be determined.

The estimated distance from the eyeball center to the cornea sphere center can be a constant approximation or may be dynamically updated.

According to some embodiments, the estimated pupil center position is determined based on the estimated eyeball center position, the estimated radius from the eyeball center to the pupil center in the eye, and the identified position of the representation of the pupil center in the obtained image by first defining an eyeball sphere having a center in the estimated eyeball center position. The eyeball sphere further has a radius of the estimated radius. Based on the identified position of the representation of the pupil center in the obtained image, a pupil ray along which the pupil center is positioned is determined. The pupil ray is a projection in three-dimensional space from the image sensor of the identified position of the representation of the pupil center in the obtained image. The estimated pupil center position is then determined as an intersection between the eyeball sphere and the pupil ray.

According to some embodiments, determining the estimated pupil center position using an iterative method taking into account refraction in a cornea of the eye from a surface of the cornea to the pupil center.

In these embodiments, refraction in the cornea is taken into account, i.e. the pupil center will not be positioned on the pupil ray being a linear projection in three-dimensional space, but the pupil ray will be refracted in the cornea of the eye.

According to some embodiments, an estimated distance from a cornea sphere center in the eye to the pupil center in the eye is obtained. An estimated cornea sphere center position is then determined as the obtained estimated distance from the cornea sphere center to the pupil center from the estimated pupil center position in the direction towards the estimated eyeball center position, i.e. starting in the estimated pupil center position and moving, in the direction from the pupil center towards the estimated eyeball center position, the obtained estimated distance from the cornea sphere center to the pupil center.

According to some embodiments the estimated cornea sphere center position can be used to predict positions of one or more glints on the eye.

In embodiments implemented in a system using a primary method for determining eye direction and/or gaze direction of an eye based on determining a pupil center in the eye and glints on the eye from one or more illuminators illuminating the eye, the estimated cornea sphere center position can be used to predict positions of one or more glints before the primary method has determined the cornea sphere center position. The prediction can then be used in associate each of the one or more glints to a corresponding illuminator of the one or more illuminators. This is useful even for a situation where there are sufficient number of glints on the eye for it is possible to determine with required reliability the position of the cornea sphere center based on the primary method.

According to some embodiments, the estimated eyeball center position is determined by determining a cornea sphere center position is determined based on one or more glint positions on the eye. Furthermore, a pupil center position is determined, and an estimated distance from the eyeball center to the cornea sphere center is obtained. The estimated eyeball center position is then determined as the estimated distance from the eyeball center to the cornea sphere center from the cornea sphere center position in a direction from the pupil center position to the cornea sphere center position, i.e. starting in the determined cornea sphere center position and moving, in the direction from the determined pupil center position to determined cornea sphere center position, the obtained estimated distance from the eyeball center to the cornea sphere center.

In embodiments implemented in a system where a primary method for determining eye direction and/or gaze direction of an eye is based on determining a pupil center in and glints on the eye from one or more illuminators illuminating the eye, the estimated eyeball center position may be determined in a situation where a sufficient number of glints are identified on the eye and the identified glints can be associated to a corresponding illuminator of the one or more illuminators, such that such that it is possible to determine with required reliability the cornea sphere center position and the eye direction. The determined sphere center position is then used together with the eye direction, and the estimated distance from the eyeball center to the cornea sphere center to determine the estimated eyeball center position. The estimated eyeball center position may then be used for situations when it is not possible to determine the eye direction and/or gaze direction with required reliability based on the primary method. Such situations are for example when an angle between a direction of the eye in relation to one or more illumination rays from the one or more illuminators becomes large, e.g. when the eye is directed to points at the edge of a display of the system. In such situations it may become difficult to identify sufficient number of glints identified on the eye and/or to associate identified glints to a corresponding illuminator of the one or more illuminators to determine with required reliability an eye direction and/or gaze direction of the eye using the primary method.

According to a second aspect, there is provided an eye tracking system comprising a circuitry configured to obtain an estimated radius from an eyeball center to a pupil center of an eye, and determine an estimated eyeball center position in the eye in relation to an image sensor for capturing images of the eye. The circuitry is further configured to obtain an image of the eye captured by means of the image sensor and determine a position of a representation of the pupil center in the eye in the obtained image is determined. The circuitry is further configured to determine an estimated pupil center position is based on the estimated eyeball center position, the estimated radius, and the identified position of the representation of the pupil center in the obtained image.

The system of the second aspect, or the circuitry comprised in such a system, may for example be configured to perform any of the embodiments of the first aspect.

Furthermore, embodiments of the system according to the second aspect may for example include features corresponding to the features of any of the embodiments of the system according to the first aspect.

According to embodiments, the eye tracking system further comprises the image sensor for capturing images of the eye.

According to embodiments, the image sensor is arranged in a wearable device.

In wearable devices, such as devices for VR and AR, where one or more image sensors are positioned on the wearable device, and hence, will not move in relation to the eye when the user moves as long as the user is wearing the device, and the eyeball center position can be approximated to be constant in relation to an image sensor capturing images of the eye regardless of the eye direction. Hence, another method based on an estimated eyeball center position can be used instead of the primary for determining an eye direction in situations where a primary method for determining eye direction and/or gaze direction is not able to produce reliable results.

According to embodiments, the circuitry is arranged in a device different from the wearable device.

According to embodiments, the circuitry is arranged in the wearable device.

According to a third aspect, there is provided one or more computer-readable storage media storing computer-executable instructions that, when executed by a computing system that implements eye/gaze data processing, cause the computing system to perform a method. The method may for example be the method according to the second aspect.

Embodiments of the one or more computer-readable storage media according to the third aspect may for example include features corresponding to the features of any of the embodiments of the method according to the first aspect.

The one or more computer-readable media may for example be one or more non-transitory computer-readable media.

It is noted that embodiments of the invention relate to all possible combinations of features recited in the claims.

Figure 1:
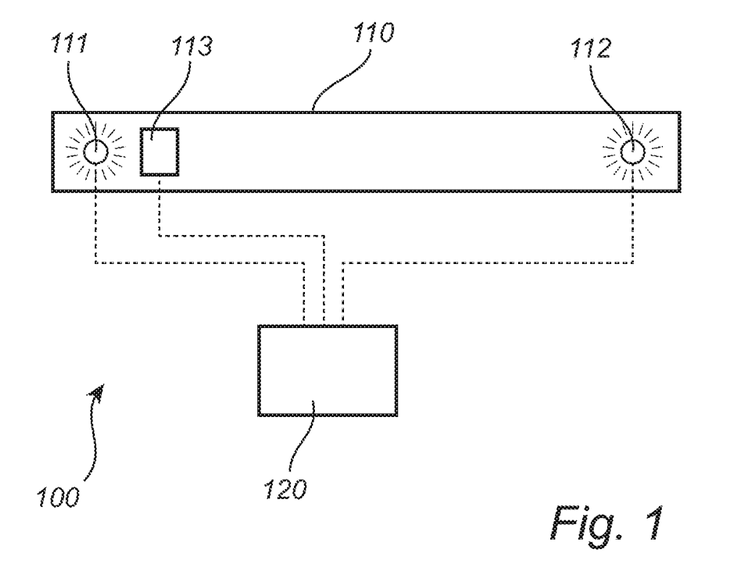
FIG. 1 shows a view of an eye tacking system, in which embodiments may be implemented.

FIG. 1 shows a simplified view of an eye tacking system 100 (which may also be referred to as a gaze tracking system) in which embodiments of the invention may be implemented. The system 100 comprises illuminators 111 and 112 for illuminating the eyes of a user, and a light sensor 113 for capturing images of the eyes of the user. The illuminators 111 and 112 may for example be light emitting diodes emitting light in the infrared frequency band, or in the near infrared frequency band. The light sensor 113 may for example be an image sensor, such as a complementary metal oxide semiconductor (CMOS) image sensor or a charged coupled device (CCD) image sensor.

A first illuminator 111 is arranged coaxially with (or close to) the light sensor 113 so that the light sensor 113 may capture bright pupil images of the user's eyes. Due to the coaxial arrangement of the first illuminator 111 and the light sensor 113, light reflected from the retina of an eye returns back out through the pupil towards the light sensor 113, so that the pupil appears brighter than the iris surrounding it in images where the first illuminator 111 illuminates the eye. A second illuminator 112 is arranged non-coaxially with (or further away from) the light sensor 113 for capturing dark pupil images. Due to the non-coaxial arrangement of the second illuminator 112 and the light sensor 113, light reflected from the retina of an eye does not reach the light sensor 113 and the pupil appears darker than the iris surrounding it in images where the second illuminator 112 illuminates the eye. The illuminators 111 and 112 may for example take turns to illuminate the eye, so that every second image is a bright pupil image, and every second image is a dark pupil image.

The eye tracking system 100 also comprises circuitry 120 (for example including one or more processors) for processing the images captured by the light sensor 113. The circuitry 120 may for example be connected to the light sensor 113 and the illuminators 111 and 112 via a wired or a wireless connection and be co-located with the light sensor 113 and the illuminators 111 and 112 or located at a distance, e.g. in a different device. In another example, circuitry 120 in the form of one or more processors may be provided in one or more stacked layers below the light sensitive surface of the light sensor 113.

Figure 2:
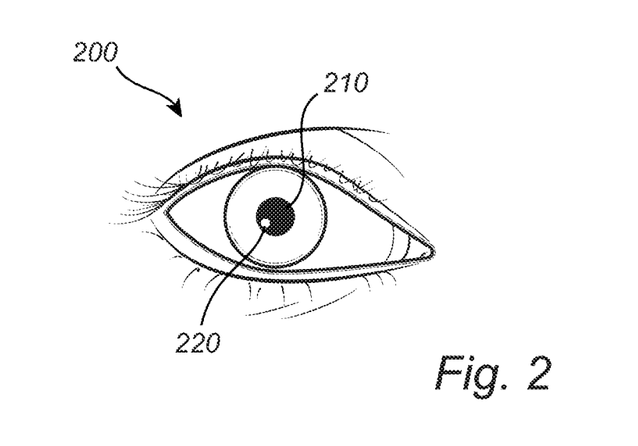
FIG. 2 shows an example image of an eye.

FIG. 2 shows an example of an image of an eye 200, captured by the light sensor 113. The circuitry 120 may for example employ image processing (such as digital image processing) for extracting features in the image. The circuitry 120 may for example employ pupil center cornea reflection (PCCR) eye tracking to determine where the eye 200 is looking. In PCCR eye tracking, the processor 120 estimates the position of the center of the pupil 210 and the position of the center of a glint 220 at the eye 200. The glint 220 is caused by reflection of light from one of the illuminators 111 and 112. The processor 120 calculates where the user is in space using the glint 220 and where the user's eye 200 is pointing using the pupil 210. Since there is typically an offset between the optical center of the eye 200 and the fovea, the processor 120 performs calibration of the fovea offset to be able to determine where the user is looking. The gaze directions obtained from the left eye and from the right eye may then be combined to form a combined estimated gaze direction (or viewing direction).

In the eye tracking system described with reference to FIG. 1, the illuminators 111 and 112 are arranged in an eye tracking module 110. This arrangement serves only as an example. It will be appreciated that more or less any number of illuminators and light sensors may be employed for eye tracking, and that such illuminators and light sensors may be distributed in many different ways relative to displays watched by the user. It will be appreciated that the eye tracking scheme described in the present disclosure may for example be employed for wearable eye tracking (such as in virtual reality (VR) glasses or augmented reality (AR) glasses).

Figure 3:
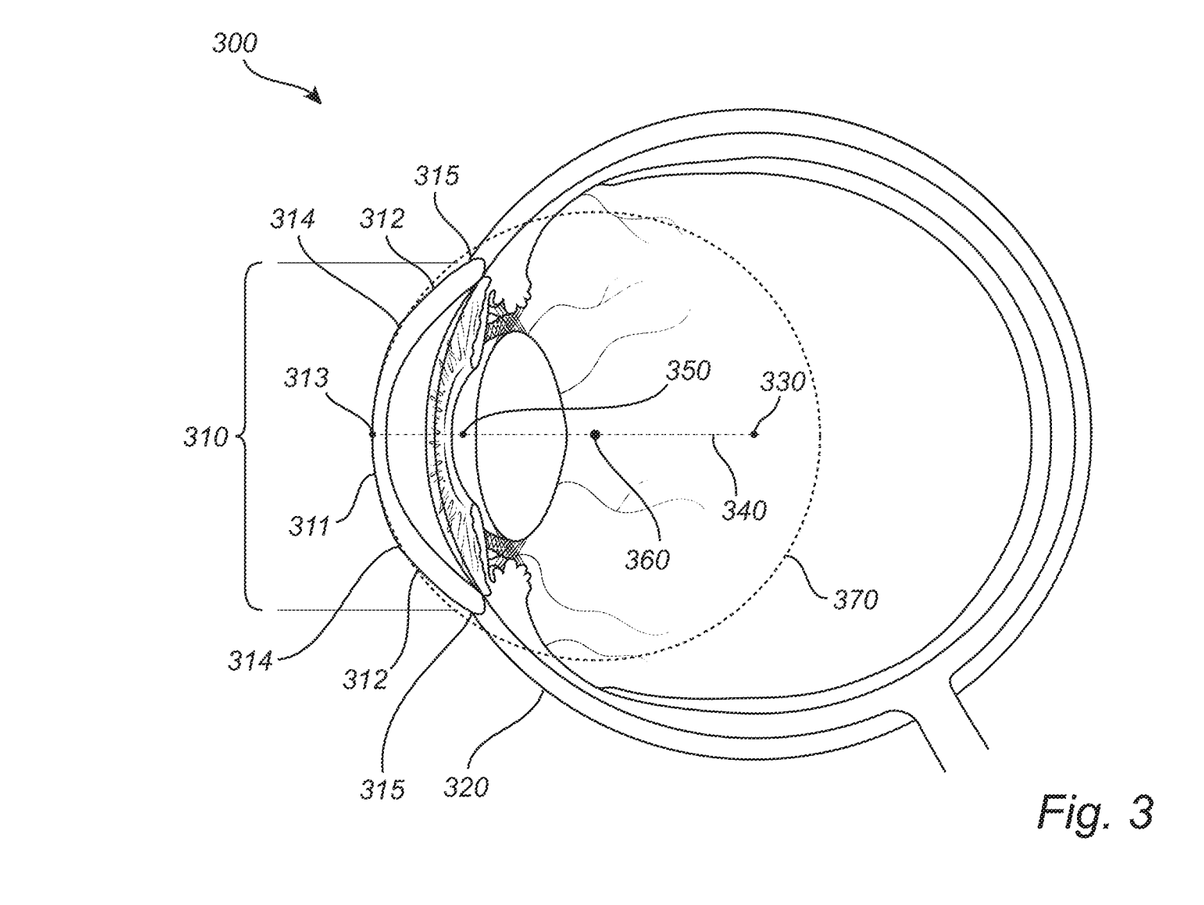
FIG. 3 is a cross sectional view of an eye.

FIG. 3 shows a cross section of different parts of an eye 300. A cornea 310 has a central region 311 which in general is close to spherical, and an outer region 312 which is non-spherical and therefore more difficult to model. The central region 311 (which is also referred to herein as the spherical region of the cornea 310) extends from a cornea surface center 313 to an edge 314 of the spherical region 311. The cornea surface center 313 is a position at the spherical region 311 of the cornea 310 where a virtual line 340 extending from an eyeball center 330 through a pupil center 350 intersects the spherical region 311 of the cornea 310. An outer region 312 of the cornea 310 extends from the edge 314 of the spherical region 311 of the cornea 310 to the edge 315 of the cornea 310. The outer region 312 is also referred to herein as the non-spherical region of the cornea 310. A cornea sphere center 360 is a position at the center of an imaginary cornea sphere 370 of which the spherical region 311 forms part. FIG. 3 also shows the sclera 320 of the eye 300.

In an eye tracking system, a current eye direction or gaze direction of the eye 300 is determined by determining the position of glints and using the geometry of the eye. In this process the current position of the cornea sphere center 360 and the current position of the pupil center 350 are determined.

Figure 4A:
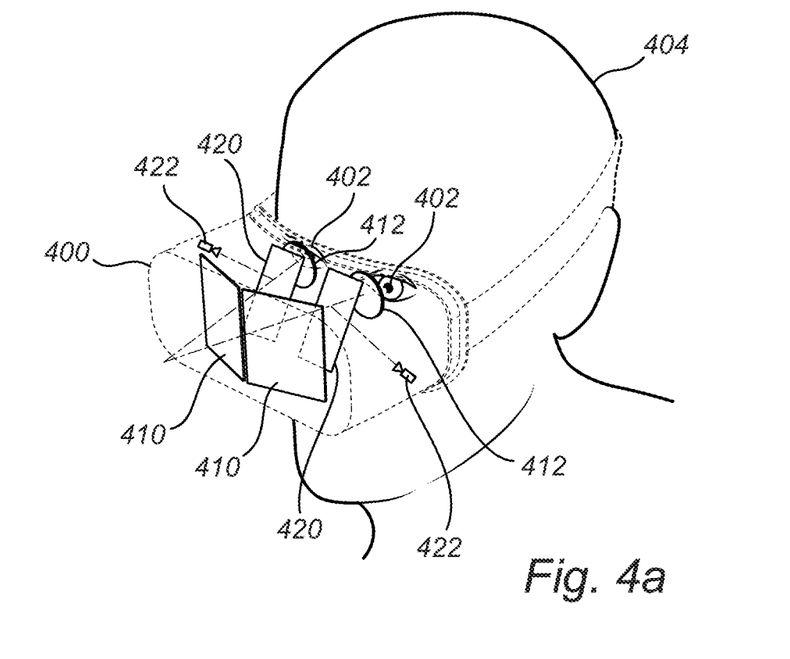
FIG. 4*a* shows a view of selected parts of a head mounted device.
Figure 4B:
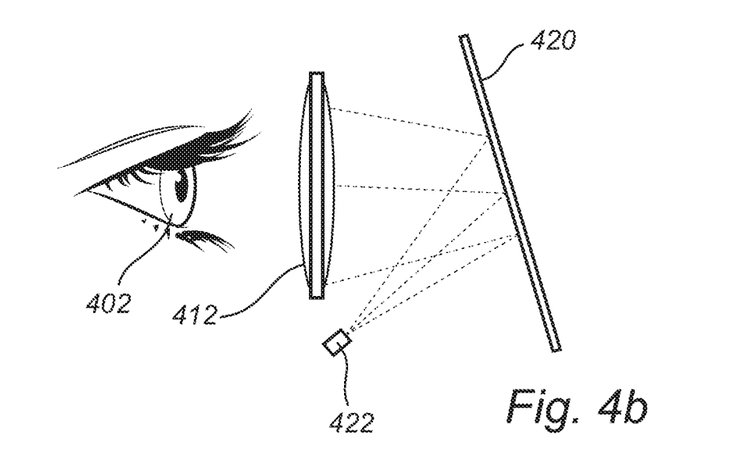
FIG. 4*b* shows a side view of selected parts of a head mounted device.
Figure 4C:
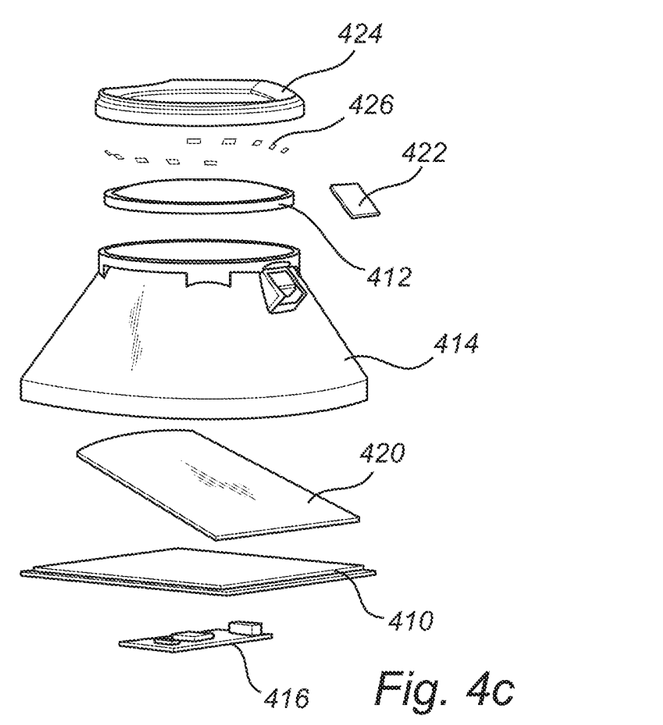
FIG. 4*c* shows an exploded view of selected parts of a head mounted device.

FIGS. 4a-c each show a separate view of selected parts of a head mounted device in the form of a virtual reality (VR) device (VR glasses) 400 including an eye tracking system in which embodiments may be implemented.

FIG. 4a shows a view of selected parts of a head mounted device in the form of the VR glasses 400 including an eye tracking system in which embodiments may be implemented. In addition to the VR glasses 400, eyes 402 and a head 404 of a user are shown. The VR portion of the VR glasses 400 shown comprises two VR displays 410 and two lenses 412, one VR display 410 and one lens 412 for each eye 402. The VR displays 410 are positioned in front of the eyes 412 and the lenses 414 are positioned between the eyes 412 and the VR displays 410. The eye tracking portion of the VR glasses 400 comprises two hot mirrors 420 and two cameras 422. In order to capture images of the eyes 412 for use in eye tracking, the hot mirrors 420 are arranged between the VR displays 410 and the lenses 414. Furthermore, illuminators (not shown) are arranged on or in the VR glasses 400 such that illumination rays are directed towards the eyes 402. Reflections from the eyes 402 of the illumination rays towards the hot mirrors 420 will reflect towards the cameras 422 in which the illumination rays are detected to produce an image of the eye. For example, the hot mirrors 420 may be of a type such that they will reflect light in the infrared frequency band but be transparent for light in the visible frequency band. The illuminators (not show) used would then produce illumination rays in the infrared frequency band and the cameras 422 will include image sensors able to detect light in the infrared frequency band.

FIG. 4b shows a side view of selected parts of the VR glasses 400. Illumination rays from the illuminators (not shown) towards the eye 402 will reflect back and pass through the lens 412 towards the hot mirror 420 and reflect towards the camera 422 in which the illumination rays are detected to produce an image of the eye.

FIG. 4c shows an exploded view of selected parts of the VR glasses 400. Selected parts for one eye are shown including an illuminator cover 424, illuminators in the form of light emitting diodes (LEDs) 426, the camera 422 including an image sensor, the lens 412, a lens cup or lens tube 414, the hot mirror 420, the VR display 410 and an electronics board 416. FIG. 4c shows an example arrangement of the illuminators in the form of LEDs 426, where the LEDs are arranged along the periphery of the lens 412 to produce a pattern when illuminating the eye 402. The illumination rays from the LEDs 426 reflected from the eye and the hot mirror is detected in the camera 422 to produce an image of the eye. Reflections on the eye (cornea) are called glints and using the position of glints, the geometry of the eye and the geometry of the setup of the VR glasses 400 are used to determine a current eye direction or gaze direction.

Head mounted devices, such as in VR glasses or augmented reality AR glasses, can be enhanced by including wearable eye tracking using illuminators and one or more light sensors arranged in the head mounted device for determining eye direction and/or gaze direction based on estimation of a position of a center of the pupil and a position of the center of one or more glints at the eye from the illuminators. A problem that can arise in such devices is that when the user watches a point close to the edge of a display, glints tend to fall off the cornea so that it becomes difficult to determine the eye direction and/or gaze direction of the user based on identification of glints.

However, even if the glints cannot be identified and used for determination of the eye direction and/or gaze direction, it may still be possible to identify the position of the center of the pupil (pupil center position).

In the following a method for determining eye direction and gaze direction will be described in relation FIG. 5a and FIG. 5b.

The method is implemented in a wearable device, such as VR glasses or AR glasses, where illuminators and image sensors are arranged on or in the wearable device, and hence, will not move in relation to the eye when the user moves as long as the user is wearing the device. In such an application, an eyeball center position can be approximated to be constant in relation to an image sensor capturing images of the eye regardless of the eye direction. The wearable device uses a primary method for determining eye direction and/or gaze direction of an eye is based on determining a pupil center in the eye and glints on the eye from the illuminators where the eye detected by means of the image sensors. An example of such a system is described in relation to FIGS. 4a-c.

In situations where a sufficient number of glints are identified on the eye and the identified glints can be associated to a corresponding illuminator of the one or more illuminators, for it to be possible to determine with required reliability the cornea sphere center position and the eye direction based on the primary method, the primary method will be used for determining eye direction and/or gaze direction.

In situations where it is not possible to determine the eye direction and/or gaze direction with required reliability based on the primary method, a secondary method for determining eye direction and/or gaze direction is used. The secondary method makes use of an estimated eyeball center position and an estimated pupil center position to determine eye direction and/or gaze direction.

The estimated eyeball center position used in the secondary method, is determined in a situation where a sufficient number of glints are identified on the eye and the identified glints can be associated to a corresponding illuminator of the illuminators, such that it is possible to determine with required reliability the cornea sphere center position and the eye direction using the primary method.

Situations where the secondary method is used are for example when an angle between a direction of the eye in relation to one or more illumination rays from the illuminators becomes large, e.g. when the eye is directed to points at the edge of a display of the system. In such situations difficulties may arise in identifying any glints or at least a sufficient number of glints on the eye, and in particular on the cornea of the eye, or that an identified glint or identified glints cannot be associated to a corresponding illuminator of the illuminators. In such a situation it may not be possible to determine with required reliability an eye direction and/or gaze direction of the eye based on the identified glint or glints using the primary method.

Situations where the primary method is used are where a sufficient number of glints are identified on the eye and the identified glints can be associated to a corresponding illuminator of the illuminators, such that it is possible to determine with required reliability the cornea sphere center position and the eye direction using the primary method.

The estimated eyeball center position may be valid only for a period of time and may then be updated at times/in situations when a sufficient number of glints are identified on the eye and the identified glints can be associated to a corresponding illuminator of the illuminators, such that it is possible to determine with required reliability the cornea sphere center position and the eye direction using the primary method.

Figure 5A:
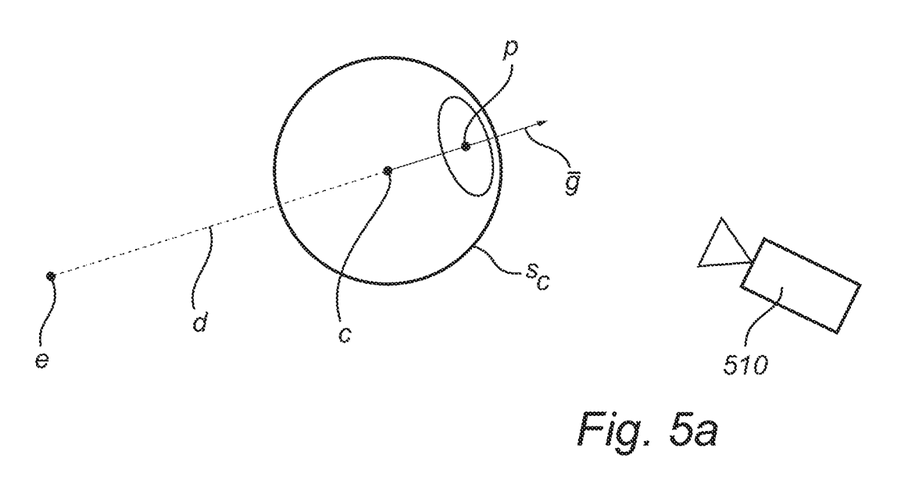
FIG. 5*a* shows a view of selected portions of the geometry of an eye in relation to embodiments.

FIG. 5a shows a view of selected portions of the geometry of an eye in relation to parts of the method for determining eye direction and gaze direction where the position of an eyeball center is estimated based on the primary method for determining eye direction and/or gaze direction. A pupil center position p, a cornea sphere center position c, a cornea sphere $s_c$, an estimated eyeball center position e, an estimated distance d from the eyeball center to the cornea sphere center, an eye direction $\bar{g}$ and a camera 510 comprising an image sensor are shown.

In relation to FIG. 5a, a situation is disclosed the angle between the between the eye direction $\hat{g}$ and one or more illumination rays from illuminators (not shown) is such that a sufficient number of glints are identified on the eye and the identified glints can be associated to a corresponding illuminator of the illuminators, for it to be possible to determine with required reliability the cornea sphere center position c and the eye direction $\bar{g}$ using the primary method.

The primary method is used to determine the cornea sphere position c based on glints on the eye as identified in an image captured by the camera 510. Furthermore, the pupil center position is determined based on a representation of the pupil center position identified in the image captured by the camera 510.

The estimated distance d from the eyeball center to the cornea sphere center is obtained as an approximation used generally for a human eye.

The eye direction $\bar{g}$ is estimated using the determined cornea sphere position c and the pupil center position p. In other words, the eye direction $\bar{g}$ is the direction from the cornea sphere center position c to the pupil center position p.

The estimated eyeball center position e can then be found based on the results of the primary method as the point on the eye direction axis the estimated distance d from the eyeball center to the cornea sphere center behind the cornea sphere center c.

As the camera 510 is arranged on or in the wearable device and the geometry of the setup of the wearable device is known, the estimated eyeball center position e in relation to the camera is known.

Figure 5B:
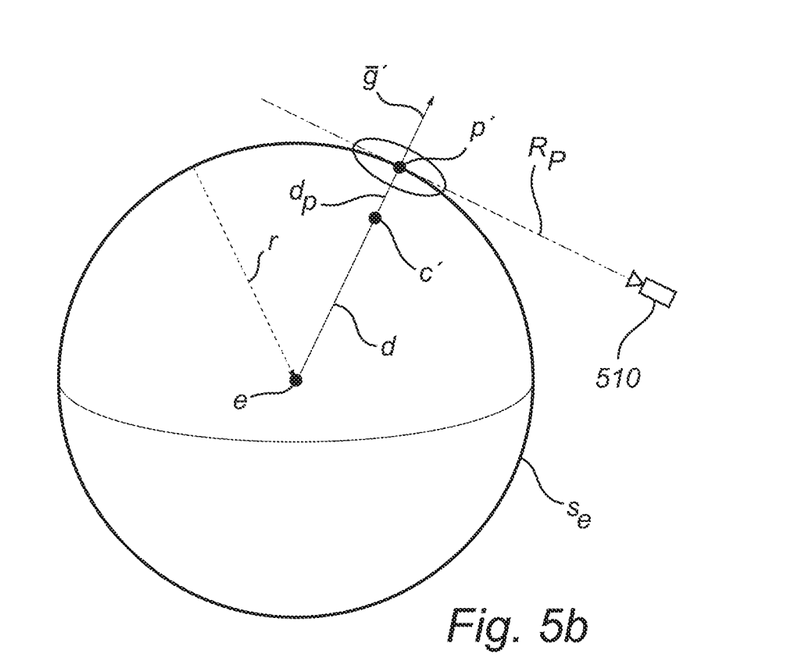
FIG. 5*b* shows a view of selected portions of the geometry of an eye in relation to embodiments.

FIG. 5b shows a view of selected portions of the geometry of an eye in relation to parts of the method for determining eye direction and gaze direction where the eye direction and/or gaze direction is determined based on the estimated eyeball center position using the secondary method. An estimated pupil center position p', an estimated cornea sphere center position c', an eyeball sphere $s_e$, an estimated eyeball center position e, an estimated radius r from the eyeball center to the pupil center, an estimated distance d from the eyeball center to the cornea center, an estimated distance $d_p$ from the cornea sphere center to the pupil center, an estimated eye direction $\bar{g}'$, an image ray $R_p$, and a camera 510 comprising an image sensor are shown.

In relation to FIG. 5b, a situation is disclosed the angle between the between the eye direction $\bar{g}'$ and one or more illumination rays from illuminators (not shown) is such that a sufficient number of glints are not identified on the eye and/or the identified glints cannot be associated to a corresponding illuminator of the illuminators, for it to be possible to determine with required reliability the cornea sphere center position c and the eye direction g using the primary method.

The estimated eyeball center position e in the eye in relation to the camera 510 has been derived as described in relation to FIG. 5*a*.

The estimated distance d from the eyeball center to the cornea sphere center and the estimated distance $d_p$ from the cornea sphere center to the pupil center are obtained as approximations used generally for a human eye.

The estimated distance $d_p$ from the cornea sphere center to the pupil center is first selected as an approximation of the distance from the cornea sphere center to the pupil center of a human eye. When further data regarding the eyes of a current user are retrieved the estimated distance $d_p$ from the cornea sphere center to the pupil center can be updated.

The eyeball sphere $s_e$ is defined as a sphere with a center in the estimated eyeball center position e with a radius r which is the sum of the estimated distance d from the eyeball center to the cornea sphere center and the estimated distance $d_p$ from the cornea sphere center to the pupil center.

An image of the eye is captured by means of the camera 510 and a position of a representation of the pupil center in the eye is identified in the image.

Based on the identified position of the representation of the pupil center in the obtained image, the pupil ray $R_p$, which is a projection in three-dimensional space, along which the pupil center is positioned. The estimated pupil center position p' is found as an intersection between the eyeball sphere $s_e$ and the pupil ray $R_p$.

An estimated eye direction $\bar{g}'$ is determined based on a vector from the estimated eyeball center position e to the estimated pupil center position p', and an estimated gaze direction can then be determined based on the estimated eye direction $\bar{g}'$.

It is to be noted that although the pupil ray $R_p$ is represented as a straight line in FIG. 5*b*, the setup of the wearable device the method is implemented in is normally such that a lens and a hot mirror are arranged between the eye and the camera 510. Hence, the projection of the identified representations in an image captured by the camera, such as the projection of the identified representation of the pupil center, in three-dimensional space need to take the known geometry of the setup and the known optical properties to identify the projection. Such a projection would then not be a straight line.

Furthermore, it is also to be noted that the use of the intersection between the pupil ray $R_p$ and the eyeball sphere $s_e$ is only an approximation. In order to more accurately determine an estimated pupil center position p', an iterative method taking into account refraction in the cornea of the eye from the cornea surface to the pupil center.

In alternative to determining an estimated eye direction and estimated gaze direction, an estimated cornea sphere center position c' can be determined using the determined estimated pupil center position p' and the obtained estimated distance $d_p$ from the cornea sphere center to the pupil center. The estimated cornea sphere center position c' is determined by moving the estimated distance $d_p$ from the cornea sphere center to the pupil center from the estimated pupil center position p' in the direction towards the estimated eyeball center position e.

The estimated cornea sphere center position c' can be used for predicting glint positions on the eye. The prediction is further based on the knowledge of the geometry of the setup of illuminators and cameras.

Figure 6:
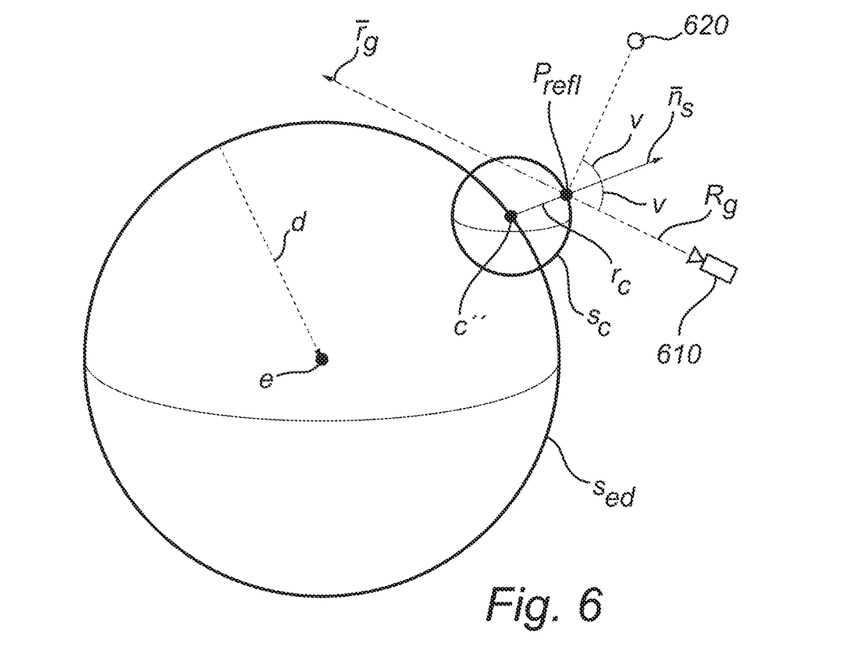
FIG. 6 shows a view of selected portions of the geometry of an eye in relation to embodiments.

FIG. 6 shows a view of selected portions of the geometry of an eye in relation to parts of a method for determining an enhanced estimated cornea center position c". A camera 610 comprising an image sensor, an illuminator 620, a glint ray $R_g$, a vector $\bar{r}_g$ from the camera which is the source of the glint ray $R_g$, a cornea surface normal $\bar{n}_s$, a reflection point $P_{refl}$, an angle v between the cornea surface normal $\bar{n}_s$ at the reflection point $P_{refl}$, an the vector $\bar{r}_g$ from the camera which is the source of the glint ray $R_g$, the enhanced estimated cornea sphere center position c", a cornea sphere $s_c$, an estimated cornea radius $r_c$ from the cornea sphere center to a cornea sphere surface, an estimated eyeball center position e, an estimated distance d from the eyeball center to the cornea sphere center, and an eyeball to cornea sphere $s_{ed}$ are shown.

In relation to FIG. 6, a situation is disclosed where one glint is identified in an image of the eye and the identified glint can be associated to a corresponding illuminator of the illuminators.

Usually a cornea center position c is estimated using two or more glints (corneal reflections) on the spherical part of the cornea surface. If there is only one glint that can be used, due to the position of the cornea relative to the camera and illuminators or due to some illuminators being obscured by the user's facial geometry, we can make use of an estimated eyeball center position e, e.g. determined such as described in relation to FIG. 5*a*, to determine an enhanced estimated cornea center position c". The enhanced estimated cornea center position c" will be more accurate than the estimated cornea center position c' as described in relation to FIG. 5*b*.

In cases where many of the glints used to position the cornea center position c are close to the edge of the cornea, where the spherical assumption is inappropriate, the enhanced estimated cornea center position c" (estimated using the glint closest to the spherical cornea "top") can also be more accurate than the cornea center position c determined by a method such as the primary method described in relation to FIG. 5*a*.

The estimated distance d from the eyeball center to the cornea sphere center is an approximation used generally for a human eye.

To calculate the enhanced estimated cornea center position c", the process below may for example be followed:

1. Position an eyeball to cornea sphere sea around the estimated eyeball center position e with a radius of the estimated distance d from the eyeball center to the cornea sphere center, the enhanced cornea sphere center position c" will be on the surface of this eyeball to cornea sphere $s_{ed}$.
2. Project the position of the identified glint in the image to the glint ray $R_g$ in three-dimensional space. The surface of the cornea sphere $s_e$ will intersect this glint ray $R_g$ at the reflection point $P_{refl}$. The cornea sphere $s_c$ is centered around the enhanced estimated cornea sphere center c" with a radius equal to the estimated cornea radius $r_c$. The cornea radius $r_c$ used is the same as is used for cornea positioning in other parts of the eye tracking method.
3. The angle v between the cornea surface normal at the reflection point $P_{refl}$ and the vector $\bar{r}_g$ from the camera which is the source of the glint ray $R_g$ and the reflection point $P_{refl}$ is the same as the angle between the cornea surface normal $\bar{n}_s$ at the reflection point $P_{refl}$ and the vector between the reflection point $P_{refl}$ and the illuminator 620 which is casting the light that caused the reflection.

4. For a given cornea sphere radius $r_c$, illuminator 620 and glint ray $R_g$, an iterative solver can find the distance along $R_g$ where the distance from the resulting cornea center (given the reflection angle constraint in 3) to the surface of $s_{ed}$ is minimized. That distance gives the reflection point $P_{refl}$ which in turn gives the enhanced estimated cornea center position c" as disclosed in FIG. 6.

Figures 7, 8, 9:
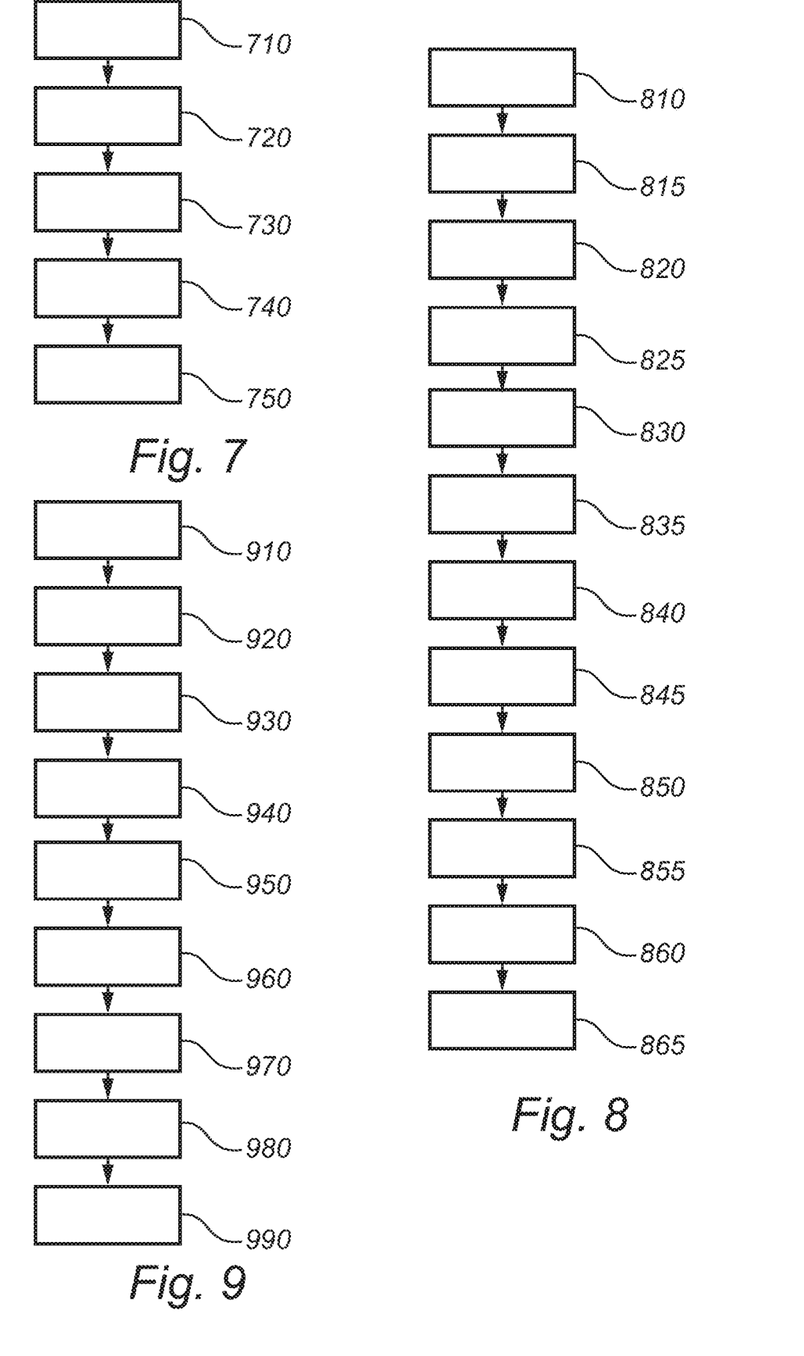
FIGS. 7-9 are flow charts of methods according to embodiments.

FIG. 7 shows a method according to an embodiment. The method comprises obtaining 710 an estimated radius r from an eyeball center to a pupil center of in an eye. The method further comprises determining 720 an estimated eyeball center position e of in the eye in relation to a camera an image sensor for capturing images of the eye, obtaining 730 an image of the eye captured by means of the camera image sensor, and identifying 740 a position of a representation of the pupil center of in the eye in the obtained image. An estimated pupil center position p' is determined 750 based on the estimated eyeball center position e, the estimated radius r, and the identified position of the representation of the pupil center in the obtained image.

FIG. 8 shows a method according to another embodiment similar to the embodiment described in relation to FIG. 7. An estimated distance $d_p$ from a cornea sphere center of in the eye to the pupil center is obtained 810, and an estimated distance d from the eyeball center to the cornea sphere center is obtained 815. An estimated radius r is equal to the sum of the estimated distance $d_p$ from the cornea sphere center to the pupil center and the estimated distance d from the eyeball center to the cornea sphere center.

A cornea sphere center position c is determined 820 based on one or more glint positions on the eye, a pupil center position p is determined 825, and an estimated eyeball center position e in relation to an image sensor is determined 830 as the estimated distance d from the eyeball center to the cornea sphere center from the cornea sphere center position c in a direction from the pupil center position p to the cornea sphere center position c. An image of the eye captured by means of the image sensor is obtained 835, and a position of a representation of the pupil center in the eye in the obtained image is identified 840. Furthermore, an eyeball sphere $s_e$ having a center in the estimated eyeball center position e and having a radius of the estimated radius r is determined 845. Based on the identified position of the representation of the pupil center in the obtained image, a pupil ray $R_p$ along which the pupil center is positioned is determined 850 and the estimated pupil center position p' is determined 855 as an intersection between the eyeball sphere $s_e$ and the pupil ray $R_p$. Based on a vector from the estimated eyeball center position e to the estimated pupil center position p', an estimated eye direction ĝ' is determined 860 and based on the estimated eye direction ĝ' an estimated gaze direction is determined 865.

The determining 855 the estimated pupil center position p' may comprise using an iterative method taking into account refraction in a cornea of the eye from a surface of the cornea to the pupil center.

FIG. 9 shows a further method according to an embodiment. The method comprises obtaining 910 an estimated radius r from an eyeball center to a pupil center of in an eye. The method further comprises determining 920 an estimated eyeball center position e of in the eye in relation to a camera an image sensor for capturing images of the eye, obtaining 930 an image of the eye captured by means of the camera image sensor, and identifying 940 a position of a representation of the pupil center of in the eye in the obtained image. An estimated pupil center position p' is determined 950 based on the estimated eyeball center position e, the estimated radius r, and the identified position of the representation of the pupil center in the obtained image. A first estimated distance $d_p$ from a cornea sphere center of in the eye to the pupil center is obtained 960, and an estimated cornea sphere center position c' is determined 970 as the first estimated distance $d_p$ from the cornea sphere center to the pupil center from the estimated pupil center position p' in the direction towards the estimated eyeball center position e. Positions of one or more glints on the eye are then predicted 980 based on estimated cornea sphere center position c'.

Figure 10:
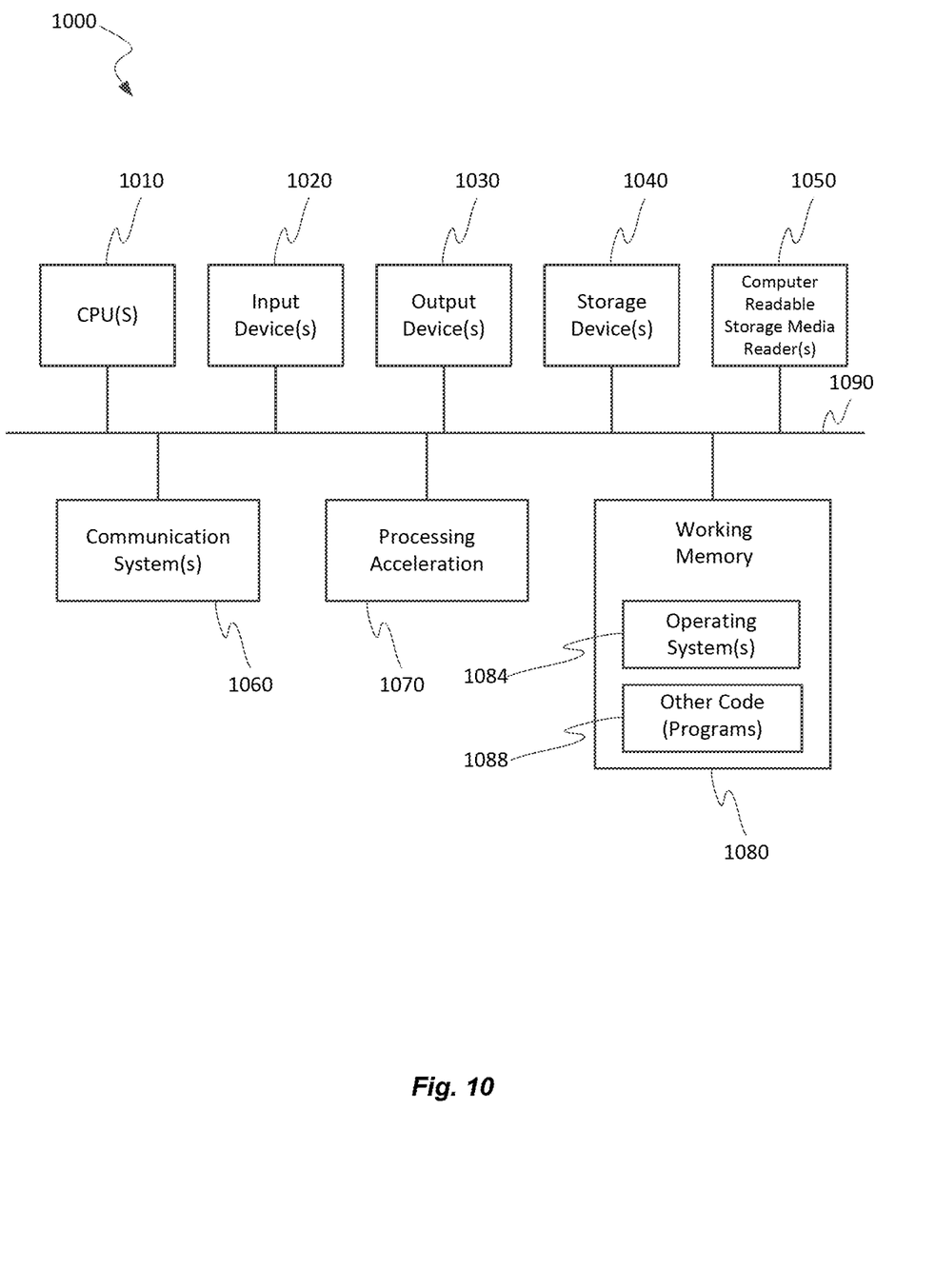
FIG. 10 is a block diagram of a specialized computer system capable of being used in at least some portion of the apparatuses or systems of the present invention, or implementing at least some portion of the methods of the present invention.

FIG. 10 is a block diagram illustrating a specialized computer system 1000 in which embodiments of the present invention may be implemented. This example illustrates specialized computer system 1000 such as may be used, in whole, in part, or with various modifications, to provide the functions of components described herein.

Specialized computer system 1000 is shown comprising hardware elements that may be electrically coupled via a bus 1090. The hardware elements may include one or more central processing units 1010, one or more input devices 1020 (e.g., a mouse, a keyboard, eye tracking device, etc.), and one or more output devices 1030 (e.g., a display device, a printer, etc.). Specialized computer system 1000 may also include one or more storage device 1040. By way of example, storage device(s) 1040 may be disk drives, optical storage devices, solid-state storage device such as a random access memory ("RAM") and/or a read-only memory ("ROM"), which can be programmable, flash-updateable and/or the like.

Specialized computer system 1000 may additionally include a computer-readable storage media reader 1050, a communications system 1060 (e.g., a modem, a network card (wireless or wired), an infra-red communication device, Bluetooth™ device, cellular communication device, etc.), and working memory 1080, which may include RAM and ROM devices as described above. In some embodiments, specialized computer system 1000 may also include a processing acceleration unit 1070, which can include a digital signal processor, a special-purpose processor and/or the like.

Computer-readable storage media reader 1050 can further be connected to a computer-readable storage medium, together (and, optionally, in combination with storage device(s) 1040) comprehensively representing remote, local, fixed, and/or removable storage devices plus storage media for temporarily and/or more permanently containing computer-readable information. Communications system 1060 may permit data to be exchanged with a network, system, computer and/or other component described above.

Specialized computer system 1000 may also comprise software elements, shown as being currently located within a working memory 1080, including an operating system 1084 and/or other code 1088. It should be appreciated that alternate embodiments of specialized computer system 1000 may have numerous variations from that described above. For example, customized hardware might also be used and/or particular elements might be implemented in hardware, software (including portable software, such as applets), or both. Furthermore, connection to other computing devices such as network input/output and data acquisition devices may also occur.

Software of specialized computer system 1000 may include code 1088 for implementing any or all of the function of the various elements of the architecture as described herein. For example, software, stored on and/or executed by a specialized computer system such as specialized computer system 1000, can provide the functions of components of the invention such as those discussed above. Methods implementable by software on some of these components have been discussed above in more detail.

A person skilled in the art realizes that the present invention is by no means limited to the preferred embodiments described above. On the contrary, many modifications and variations are possible within the scope of the appended claims. For example, the person skilled in the art realizes that the eye/gaze tracking methods described herein may be performed by many other eye/gaze tracking systems than the example eye/gaze tracking system 100 shown in FIG. 100, for example using multiple illuminators and multiple image sensors such as shown e.g. in FIGS. 4*a-c*.

Additionally, variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The division of tasks between functional units referred to in the present disclosure does not necessarily correspond to the division into physical units; to the contrary, one physical component may have multiple functionalities, and one task may be carried out in a distributed fashion, by several physical components in cooperation. A computer program may be stored/distributed on a suitable non-transitory medium, such as an optical storage medium or a solid-state medium supplied together with or as part of other hardware, but may also be distributed in other forms, such as via the Internet or other wired or wireless telecommunication systems. The mere fact that certain measures/features are recited in mutually different dependent claims does not indicate that a combination of these measures/features cannot be used to advantage. Method steps need not necessarily be performed in the order in which they appear in the claims or in the embodiments described herein, unless it is explicitly described that a certain order is required. Any reference signs in the claims should not be construed as limiting the scope.

What is claimed is:

1. A method comprising:
    obtaining an estimated radius (r) from an eyeball center to a pupil center in an eye;
    determining an estimated eyeball center position (e) in the eye in relation to an image sensor for capturing images of the eye;
    obtaining an image of the eye captured by means of the image sensor;
    identifying a position of a representation of the pupil center in the eye in the obtained image; and
    determining an estimated pupil center position (p') based on the estimated eyeball center position (e), the estimated radius (r), and the identified position of the representation of the pupil center in the obtained image.

2. The method of claim 1, further comprising:
    determining an estimated eye direction (ĝ') based on a vector from the estimated eyeball center position (e) to the estimated pupil center position (p').

3. The method of claim 2, further comprising:
    determining an estimated gaze direction based on the estimated eye direction (ĝ').

4. The method of claim 1, wherein obtaining an estimated radius (r) comprises:
    obtaining an estimated distance (dp) from a cornea sphere center in the eye to the pupil center; and
    obtaining an estimated distance (d) from the eyeball center to the cornea sphere center,
    wherein the estimated radius (r) is equal to the sum of the estimated distance (dp) from the cornea sphere center to the pupil center and the second estimated distance (d) from the eyeball center to the cornea sphere center.

5. The method of claim 1, wherein determining the estimated pupil center position (p') comprises:
    determining an eyeball sphere (se) having a center in the estimated eyeball center position (e) and having a radius of the estimated radius (r);
    determining, based on the identified position of the representation of the pupil center in the obtained image, a pupil ray (Rp) along which the pupil center is positioned; and
    determining the estimated pupil center position (p') as an intersection between the eyeball sphere (se) and the pupil ray (Rp).

6. The method of claim 5, further comprising:
    determining the estimated pupil center position (p') using an iterative method taking into account refraction in a cornea of the eye from a surface of the cornea to the pupil center.

7. The method of claim 1, further comprising:
    obtaining an estimated distance (dp) from a cornea sphere center in the eye to the pupil center; and
    determining an estimated cornea sphere center position (c') as the estimated distance (dp) from the cornea sphere center to the pupil center from the estimated pupil center position (p') in the direction towards the estimated eyeball center position (e).

8. The method of claim 7, further comprising:
    predicting positions of one or more glints on the eye based on the estimated cornea sphere center position (c').

9. The method of claim 1, wherein determining an estimated eyeball center position (e) in the eye in relation to an image sensor for capturing images of the eye comprises:
    determining a cornea sphere center position (c) based on one or more glint positions on the eye;
    determining a pupil center position (p);
    obtaining an estimated distance (d) from the eyeball center to the cornea sphere center; and
    determining an estimated eyeball center position (e) as the estimated distance (d) from the eyeball center to the cornea sphere center from the cornea sphere center position (c) in a direction from the pupil center position (p) to the cornea sphere center position (c).

10. An eye tracking system comprising a circuitry configured to perform the method of claim 1.

11. The eye tracking system of claim 10, further comprising the image sensor for capturing images of the eye.

12. The eye tracking system of claim 11, wherein the image sensor is arranged in a wearable device.

13. The eye tracking system of claim 12, wherein the circuitry is arranged in a device different from the wearable device.

14. The eye tracking system of claim 12, wherein the circuitry is arranged in the wearable device.

15. One or more tangible non-transitory computer-readable storage media storing computer-executable instructions that, when executed by a computing system that implements eye/gaze data processing, cause the computing system to perform a method, the method comprising:
    obtaining an estimated radius (r) from an eyeball center to a pupil center in an eye;
    determining an estimated eyeball center position (e) in the eye in relation to an image sensor for capturing images of the eye;

obtaining an image of the eye captured by means of the image sensor;

identifying a position of a representation of the pupil center in the eye in the obtained image; and determining an estimated pupil center position (p') based on the estimated eyeball center position (e), the estimated radius (r), and the identified position of the representation of the pupil center in the obtained image.

16. One or more tangible non-transitory computer-readable storage media storing computer-executable instructions that, when executed by a computing system that implements eye/gaze data processing, cause the computing system to perform the method of one of claim 1.

\* \* \* \* \*